United States Patent [19]

Snichelotto

[11] Patent Number: 5,443,491
[45] Date of Patent: Aug. 22, 1995

[54] THREE-POLE ELECTROCATHETER

[75] Inventor: Eugenio Snichelotto, Padova, Italy

[73] Assignee: M.E.D.I.C.O. Italia S.r.l., Padova, Italy

[21] Appl. No.: 302,966

[22] Filed: Sep. 12, 1994

Related U.S. Application Data

[63] Continuation of Ser. No. 984,624, Dec. 2, 1992, abandoned.

[30] Foreign Application Priority Data

Dec. 16, 1991 [EP] European Pat. Off. ........... 91121508

[51] Int. Cl.⁶ .............................................. A61N 1/05
[52] U.S. Cl. .................................................. 607/122
[58] Field of Search .............. 128/642; 607/116, 119, 607/122, 123, 126–128, 132

[56] References Cited

U.S. PATENT DOCUMENTS

| | | | |
|---|---|---|---|
| 4,355,646 | 10/1982 | Kallok et al. | 607/122 |
| 4,784,161 | 11/1988 | Skalsky et al. | 607/116 |
| 4,860,446 | 8/1989 | Lessar et al. | 607/119 |
| 5,007,435 | 4/1991 | Doan et al. | 607/119 |

Primary Examiner—Lee S. Cohen
Assistant Examiner—Jeffrey R. Jastrzab
Attorney, Agent, or Firm—Guido Modiano; Albert Josif

[57] ABSTRACT

An implantable improved three-pole electrocatheter for permanent cardiac stimulation. The electrocatheter is of the type which comprises a flexible body which extends predominantly axially, is made of biocompatible material and can be surgically inserted through a vein until it reaches the cardiac muscle with a terminal portion. The terminal portion is equipped with a ventricular electrode at its end and has, on its outer surface, a pair of atrial electrodes which are appropriately spaced from one another and with respect to the ventricular electrode. On the side opposite to the terminal portion, the flexible body is provided with connections which are electrically connected to the atrial and ventricular electrodes. The electrocatheter is characterized in that the electric connections comprise a three-pole connector to which the electrodes are connected by means of coiled insulated conductors. The coils defined by the conductors are coaxial.

18 Claims, 3 Drawing Sheets

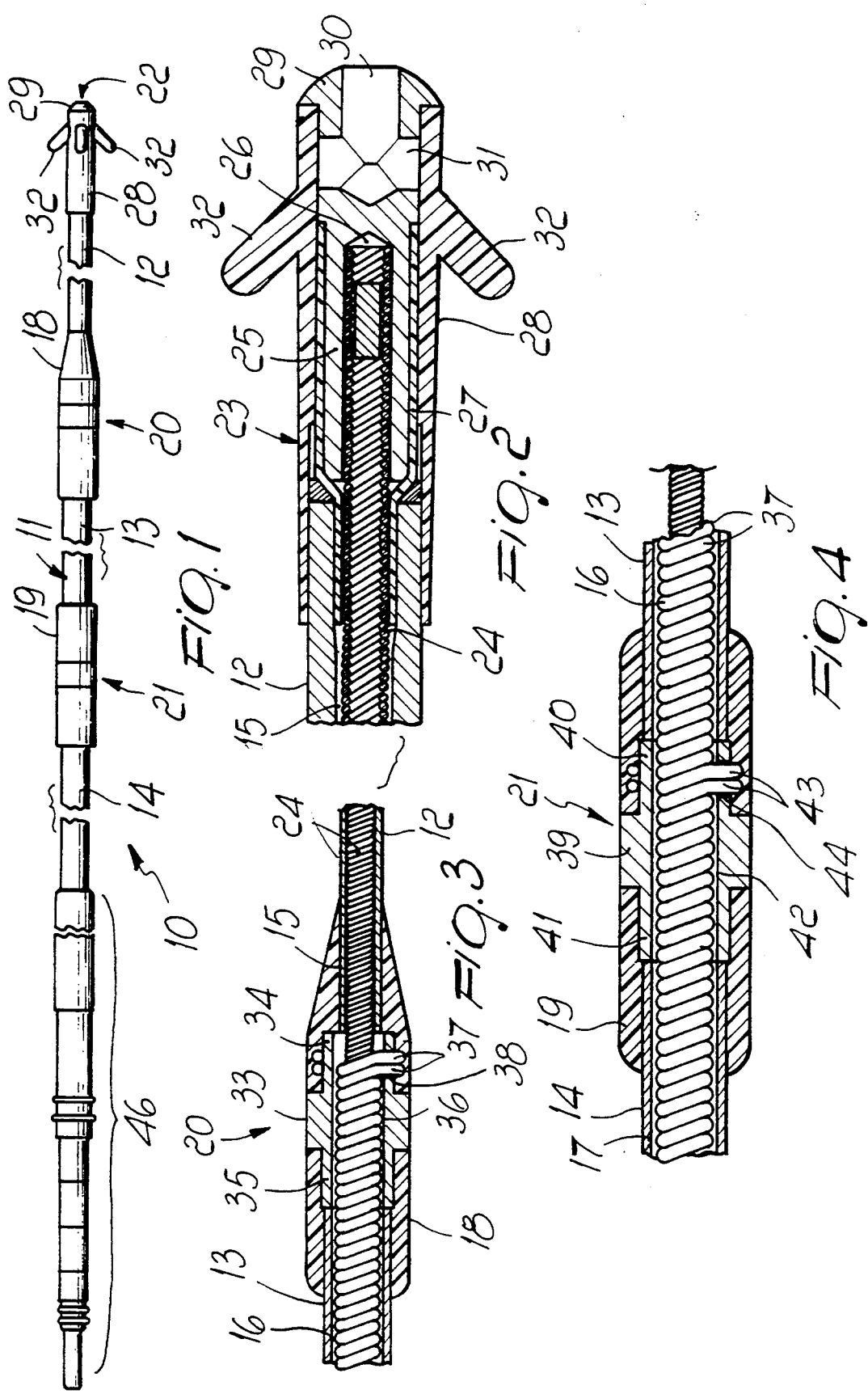

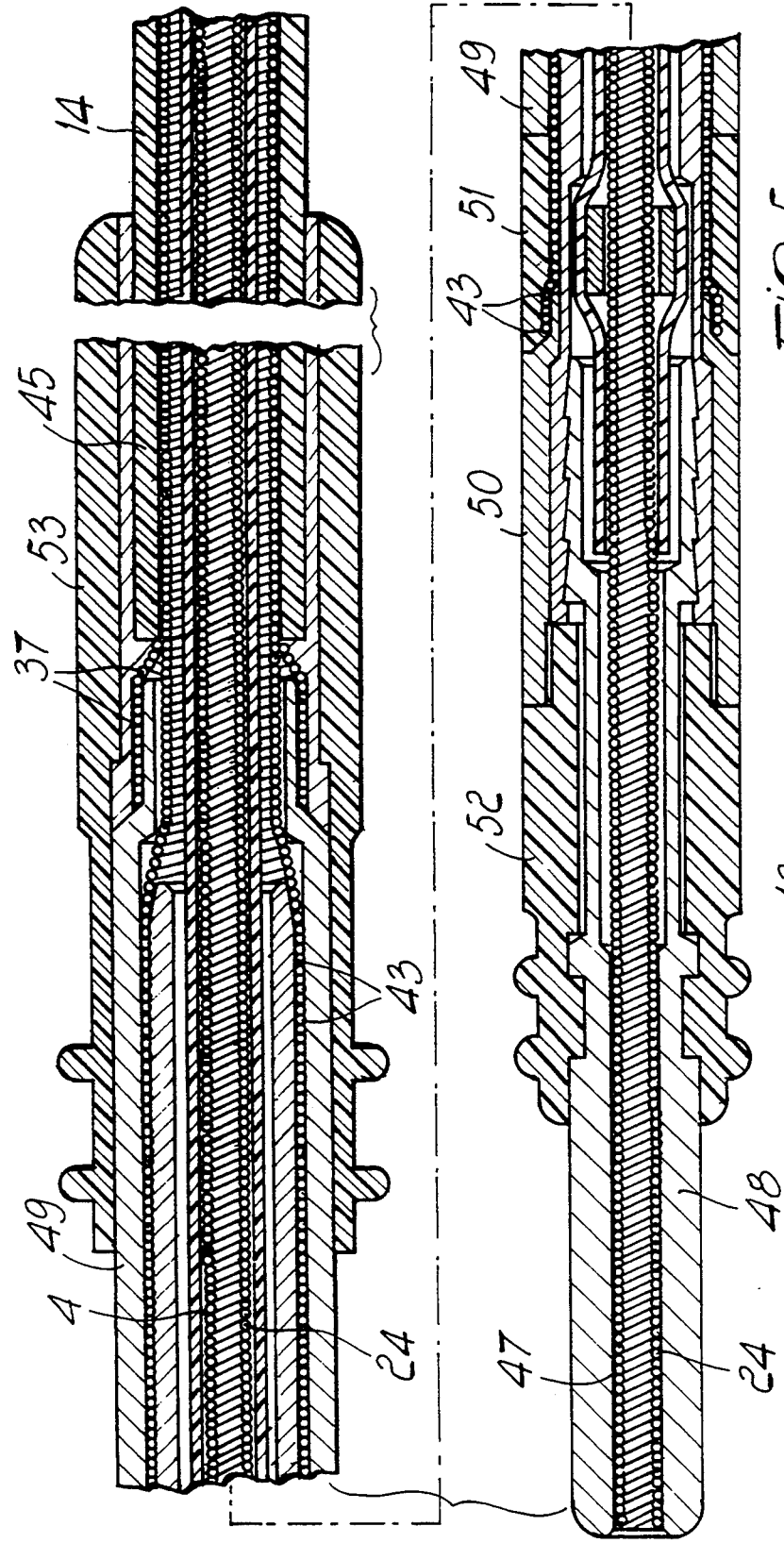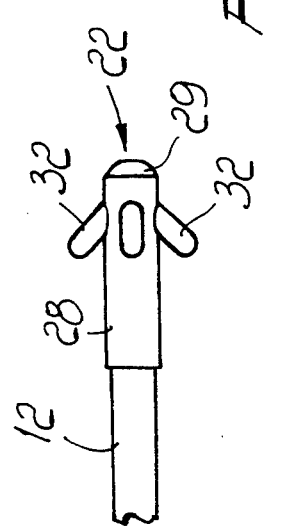

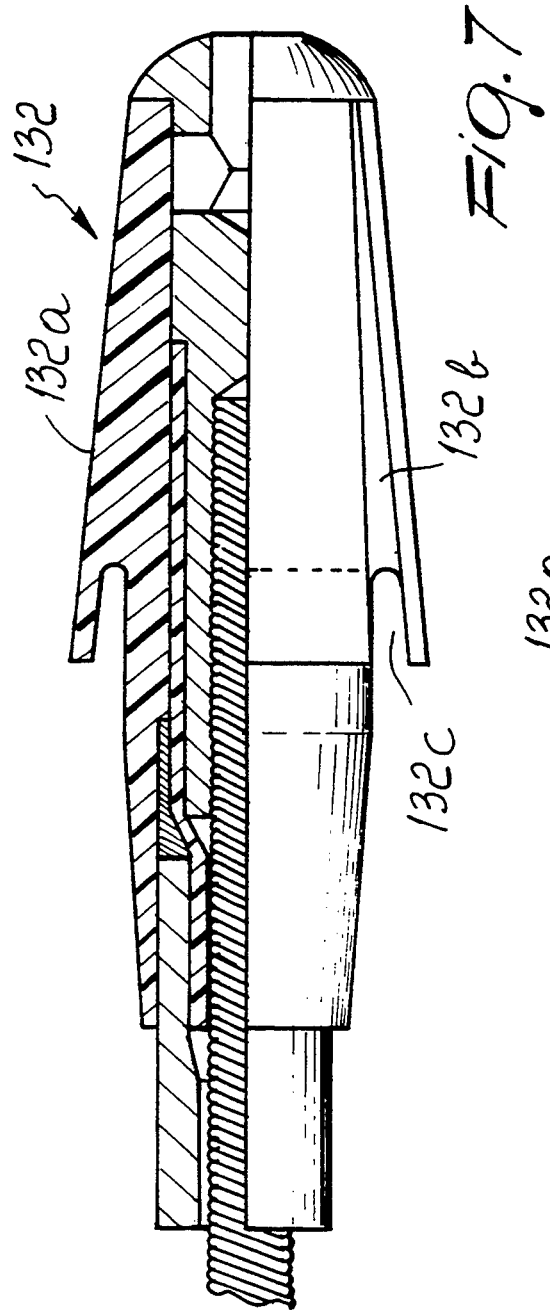
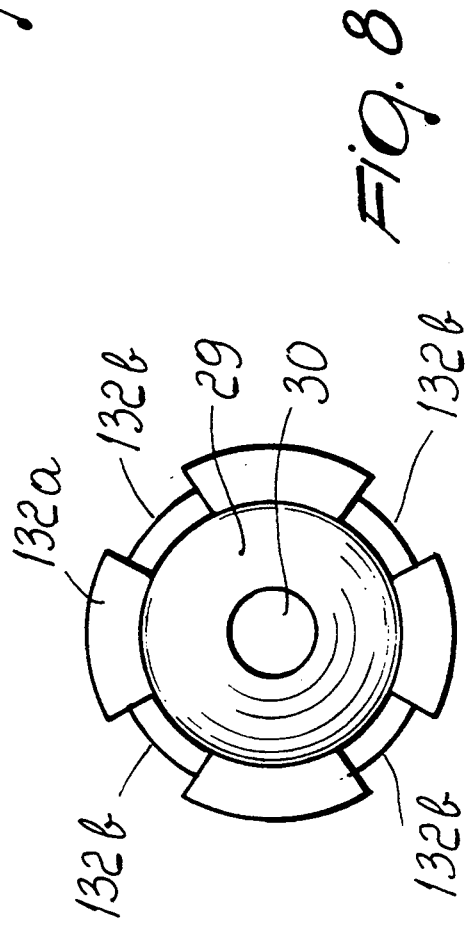

THREE-POLE ELECTROCATHETER

This is a continuation application of Ser. No. 07/984,624 filed on Dec. 2, 1992, now abandoned.

BACKGROUND OF THE INVENTION

The present invention relates to an improved three-pole electrocatheter for permanent cardiac stimulation.

Among the various known methods for permanent electric cardiac stimulation, the method which entails the detection of the spontaneous atrial signal and the consequent activation of the appropriately delayed ventricle stimulation circuit is particularly useful in the treatment of some diseases of the cardiac conduction system.

This stimulation method, known as "atrium-guided" has the invaluable advantage of adapting the ventricular stimulation frequency to the sinus frequency.

In order to perform this stimulation it is therefore necessary to provide both a detection system, suitable for receiving the signal generated by atrial activation, and a system which carries the electric signal, processed by the cardiac stimulator, to the ventricular tissue, with the additional capability, as in the conventional ventricle-inhibited method, of also receiving the ventricular spontaneous activation signal.

In order to perform this stimulation method, three-pole electrocatheters are already in use and are substantially constituted by a flexible body which extends substantially axially; a terminal portion of said body has a ventricular electrode at its end and has, on its own outer surface, a pair of atrial electrodes which are appropriately spaced from one another and with respect to the ventricular electrode.

On the side opposite to the terminal portion, the flexible body is divided into two terminal sections which also extend substantially axially and respectively bear a unipolar pin and a bipolar pin, both of which can be connected to an adapted cardiac stimulator.

The unipolar pin and the bipolar pin are electrically connected, by mutually adjacent and electrically insulated coiled electric conductors which extend inside the flexible body, respectively to the ventricular electrode and to the pair of atrial electrodes in order to receive the spontaneous atrial signal and accordingly stimulate the ventricle.

However, this known electrocatheter is not free from disadvantages, including most of all the fact that the structure of the flexible body, by having three adjacent coiled electric conductors along most of its extension, has a cross-section which is not adequate for all or most applicative requirements.

The fact that it is necessary to provide thickness changes which are as uniform and as carefully blended as possible has furthermore produced a certain complication in the internal structure of the electrocatheter, in particular in the electrode regions, to the detriment of the production process and accordingly of costs.

SUMMARY OF THE INVENTION

The aim of the present invention is to provide a three-pole electrocatheter which eliminates the disadvantages described above in known types.

A consequent primary object is to provide an electrocatheter which, despite achieving advanced functional characteristics, has a simplified structure and a reduced bulk, so as to technically facilitate the related surgical implantation.

Not least object is to provide a three-pole electrocatheter which, by virtue of its peculiar characteristics, is capable of giving the greatest assurances of reliability and safety in use.

This aim, these objects and others which will become apparent hereinafter are achieved by an improved three-pole electrocatheter for permanent cardiac stimulation, according to the present invention, as defined in the appended claims.

BRIEF DESCRIPTION OF THE DRAWINGS

Further characteristics and advantages of the invention will become apparent from the detailed description of an embodiment thereof, illustrated only by way of non-limitative example in the accompanying drawings, wherein:

FIG. 1 is a perspective view of a three-pole catheter according to the present invention;

FIG. 2 is an enlarged sectional detail view of the structure of the ventricular electrode;

FIG. 3 is an enlarged sectional detail view of the structure of the atrial proximal electrode;

FIG. 4 is an enlarged sectional detail view of the structure of the atrial distal electrode;

FIG. 5 is a longitudinal sectional view of the structure of the three-pole pin supported by the electrocatheter at one of its ends;

FIG. 6 is a view of the head of the ventricular electrode of FIG. 2;

FIG. 7 is a lateral view of a further embodiment of the head of the ventricular electrode;

FIG. 8 is a front view of the head of FIG. 7.

DESCRIPTION OF THE PREFERRED EMBODIMENTS

With reference to the above figures, a three-pole electrocatheter for permanent cardiac stimulation, generally indicated by the reference numeral 10, comprises an outer flexible body 11 which is composed of three segments, respectively a first segment 12, a second segment 13 and a third segment 14, which extend substantially axially and are conveniently manufactured by means of an extrusion process from a biocompatible material with adequate dielectric characteristics, for example medical-grade silicone or polyurethane.

The three segments 12, 13 and 14 are axially crossed by respective holes or "ports" indicated by 15, 16 and 17, in which coiled insulated electric conductors are arranged; said conductors are advantageously made of a metallic alloy having high bioelectric properties, such as for example elgiloi or mp35; said segments are mutually connected between two silicone shells i.e. a first shell 18 and a second shell 19 which respectively contain the proximal atrial electrode 20 and the distal atrial electrode 21 and which seal and reinforce the joints.

The ventricular electrode 22 is instead arranged at the first end 23 of the segment 12.

The first segment 12 is crossed by a single conductor 24 and has a length which is appropriately chosen within a range of values comprised between 10 and 15 cm.

As shown in FIG. 2, the ventricular electrode 22 has a substantially cylindrical body 25 which is inserted in the end 23 and which has an axial dead hole 26 in which the ventricular conductor 24 is crimped.

The body 25 and a portion of the conductor 24 are surrounded by a tubular element 27 which is suitable for improving their coupling.

The end 23 and the ventricular electrode 22 are contained in a silicone third shell 28 which seals and reinforces the joint.

The ventricular electrode 22 protrudes from the silicone shell 28 with a rounded head 29 which has an internal cavity formed by an axial opening 30 blended with a transverse hole 31 inside which the silicone material is inserted, obtaining a safe grip of said electrode.

Inclined barbs 32 extend from the silicone shell 28 which are arranged along radial planes and which are suitable for constituting an active securing system which ensures the stability of the ventricular electrode 22.

The proximal atrial electrode 20 is interposed between the second end of the first segment 12 and the first end of the second segment 13, and as illustrated in FIG. 3, such electrode 20 has a larger-diameter cylindrical portion 33 from which respective smaller-diameter cylindrical portions 34 and 35 extend coaxially toward the first segment 12 and the second segment 13.

The portion 33 protrudes from the silicone shell 18 in which said proximal electrode 20 is contained, thus defining an element for electric contact with hematic fluid.

The proximal atrial electrode 20 is axially crossed by a hole 36; the end of the two-start coil formed by a pair of insulated conductors 37 which surrounds the conductor 24 enters said hole.

The conductors 37 end at the cylindrical portion 34, through which they pass in an adapted hole 38 and to which they are electrically connected.

The hole 16 of the second segment 13 is thus crossed both by the conductor 24 and by the pair of conductors 37 wrapped around it.

The distal electrode 21 is interposed between the second end of the second segment 13 and the first end of the third segment 14; as shown in FIG. 4, said distal electrode has a larger-diameter cylindrical portion 39 from which respective smaller-diameter cylindrical portions 40 and 41 extend toward the second segment 13 and toward the third segment 14.

The larger-diameter cylindrical portion 39 protrudes from the silicone shell 19 which contains the distal electrode 21 and the ends of the segments 13 and 14.

The portion 39 therefore constitutes an element for electric contact with the hematic column.

The electrode 21 is axially provided with a hole 42 which is crossed by the conductor 24, by the conductors 37 and by a pair of insulated conductors 43 which are integrated in the same coil defined by the conductors 37.

The conductors 43 end at the cylindrical portion 40, which they cross in an adapted hole 44 and to which they are electrically connected.

The hole 17 of the third segment 14 is thus crossed by a first coil, formed by the conductor 24, and by a second four-conductor coil formed by the pair of conductors 37 and by the pair of conductors 43 and surrounding the first coil.

The second end 45 of the third segment 14, which is on the opposite side with respect to the terminal portion affected by the electrodes, is integrated with a three-pole connector 46 which has electric contacts to which the various conductors which arrive respectively from the ventricular electrode 22, from the distal electrode 21 and from the proximal electrode 20 are connected.

In particular, with reference to FIG. 5, the conductor 24 is inserted in an axial hole 47 of an end pin 48 to which it is electrically connected, whereas the pair of conductors 37 and 43 end at conducting rings, respectively 49 and 50, to which they are electrically connected and which protrude circumferentially from the wall of the connector 46.

Conveniently, the bands 49 and 50 and the pin 48 are mutually insulated by means of insulating elements 51 and 52.

Advantageously, the assembly is shaped so that the various elements grip one another and form a single unit.

The end of the connector 46 into which the end 45 of the third segment 14 is inserted is partially contained in a silicone shell 53 which constitutes a grip element for inserting said connector in a coupling which is present in an adapted cardiac stimulator.

From what has been described above, the operation of an electrocatheter 10 according to the invention is evident and can be summarized as follows.

The catheter is surgically inserted through a vein of the patient so as to place the electrodes inside the cardiac muscle, with the ventricular electrode 22 in contact with the bottom of the ventricle and with the two atrial electrodes 20 and 21 at the overlying atrium; the three-pole connector is then connected to a respective coupling provided in the adapted cardiac stimulator.

The two atrial electrodes 20 and 21 are thus capable of detecting the atrial activation potentials directly through the hematic fluid column, with no need for contact with the walls of the heart.

The proximal electrode 20 detects the greater activation wave, whereas the distal electrode 21 detects the smaller one, so that an average atrial signal is always received between the two electrodes 20 and 21 and in practice has a value approximately comprised between 0.5 and 2 millivolts.

According to the signal received by the atrial electrodes, the stimulator sends, after an appropriate time interval, by means of the ventricular electrode 22, an electric pulse suitable for stimulating the ventricle.

The ventricular electrode 22 furthermore detects the spontaneous potentials of the ventricle and transmits them to the stimulator so that they can be processed in order to obtain a "ventricle-inhibited" stimulation mode.

The electrocatheter is thus able to provide the "atrium-guided" and "ventricle-inhibited" cardiac stimulation mode.

The shape and particular mutual arrangement of the electrodes, as well as of the conductors which connect said electrodes and the three-pole connector, have allowed to optimize space occupation and to considerably reduce the cross-section with respect to known types of electrocatheters used so far.

The invention thus conceived is susceptible to numerous modifications and variations, all of which are within the scope of the inventive concept.

Thus, for example, with particular reference to the above mentioned FIGS. 7 and 8, the barbs 32 may be replaced with a rostrum 132 with a frustrum-shaped outer surface 132a which is longitudinally crossed for example by four channels 132b which are arranged angularly at 90° with respect to one another.

The base of the rostrum 132 is furthermore crossed by an annular channel 132c proximate to its edge.

The rostrum can in turn be replaced with another passive fixing system or even by an active fixing system, for example one with a retractable screw.

In practice, the materials employed, so long as compatible with the contingent use, as well as the dimensions, may be any according to the requirements and to the state of the art.

I claim:

1. An improved three-pole electrocatheter for permanent cardiac stimulation, comprising:

a flexible body of biocompatible material, comprising a first segment, a second segment and a third segment which extend successively and substantially axially, the first segment defining a first end of the first segment and a second end of the first segment, the second segment defining a first end of the second segment and a second end of the second segment and the third segment defining a first and a second end of the third segment;

a ventricular electrode provided at the first end of the first segment;

a first shell connecting the second end of the first segment to the first end of the second segment;

a proximal atrial electrode accommodated in the first shell;

a second shell connecting the second end of the second segment to the first end of the third segment;

a distal atrial electrode accommodated in the second shell;

axial holes provided within the first, the second and the third segment;

coaxial coiled insulated electric conductors extending through the axial holes;

a three-pole connector provided at the second end of the third segment and connected to the electrodes by the coiled insulated electric conductors, wherein said proximal atrial electrode has a larger-diameter cylindrical portion which protrudes from the first shell and two smaller-diameter cylindrical portions which extend axially from the larger-diameter cylindrical portion towards the first and the second segments respectively and are contained in the first shell, said cylindrical portions being axially crossed by a hole, a first pair of said electric conductors passing through the hole and ending at one of said smaller-diameter cylindrical portions, an adapted hole being radially provided in said one of the smaller-diameter cylindrical portions, the first pair of electric conductors passing through the adapted hole and being electrically connected to said one of said smaller-diameter cylindrical portions.

2. The electrocatheter according to claim 1 wherein said segments are obtained by extrusion from a material selected from the group consisting of medical-grade silicon and polyurethane.

3. The electrocatheter according to claim 1, wherein one of the electric conductors is connected to the ventricular electrode and defines a first coil and wherein said first pair and a second pair of the electric conductors are connected to the proximal and distal atrial electrodes respectively and are integrated in a second coil, said second coil surrounding the first coil.

4. The electrocatheter according to claim 1 wherein said three-pole connector comprises a body having a cylindrical extension with an axial end pin electrically connected to said ventricular electrode and two conducting rings which are spaced and insulated from one another and from said pin, each of said rings being electrically connected to one of said atrial electrodes.

5. The electrocatheter according to claim 1, wherein said distal atrial electrode comprises a larger-diameter cylindrical portion which protrudes from the second shell, and two smaller-diameter cylindrical portions which extend axially from the larger-diameter cylindrical portion towards the second and the third segments respectively, and are contained in the second shell, said cylindrical portions being axially crossed by a hole, the coiled insulated electric conductors passing through the hole, an adapted hole being radially provided in one of the smaller-diameter cylindrical portions, a second pair of said conductors passing through the adapted hole and being electrically connected to said one of said smaller-diameter cylindrical portions.

6. The electrocatheter according to claim 1, wherein said ventricular electrode has a substantially cylindrical body inserted in a tubular element inserted in the first end of the first segment, a third shell being provided around the first end of the first segment and around the cylindrical body for sealingly connecting the first end of the first segment to the ventricular electrode, a rounded head extending from said cylindrical body outside the third shell, said head having an inner cavity filled with silicone material, said cylindrical body having an axial dead hole, one of the electric conductors ending in said dead hole and being electrically connected to the cylindrical body.

7. An improved three-pole electrocatheter for permanent cardiac stimulation, comprising:

a flexible body of biocompatible material, comprising a first segment, a second segment and a third segment which extend successively and substantially axially, the first segment defining a first end of the first segment and a second end of the first segment, the second segment defining a first end of the second segment and a second end of the second segment and the third segment defining a first and a second end of the third segment;

a ventricular electrode provided at the first end of the first segment;

a first shell connecting the second end of the first segment to the first end of the second segment;

a proximal atrial electrode accommodated in the first shell;

a second shell connecting the second end of the second segment to the first end of the third segment;

a distal atrial electrode accommodated in the second shell;

axial holes provided within the first, the second and the third segment;

coaxial coiled insulated electric conductors extending through the axial holes;

a three-pole connector provided at the second end of the third segment and connected to the electrodes by the coiled insulated electric conductors, wherein said distal atrail electrode comprises a larger-diameter cylindrical portion which protrudes from the second shell, and two smaller-diameter cylindrical portions which extend axially from the larger-diameter cylindrical portion towards the second and the third segments respectively, and are contained in the second shell, said cylindrical portions being axially crossed by a hole, the coiled insulated electric conductors passing through the hole, an adapted hole being radially provided in one of the smaller-diameter cylindrical portions, a first pair of said conductors passing through the adapted hole and being electrically connected to said one of said smaller-diamter cylindrical portions.

8. The electrocatheter according to claim 7, wherein said segments are obtained by extrusion from a material selected from the group consisting of medical-grade silicon and polyurethane.

9. The electrocatheter according to claim 7, wherein said proximal atrial electrode has a larger-diameter cylindrical portion which protrudes from the first shell and two smaller-diameter cylindrical portions which extend axially from the larger-diameter cylindrical portion towards the first and the second segments respectively and are contained in the first shell, said cylindrical portions being axially crossed by a hole, said first pair of said electric conductors passing through the hole and ending at one of said smaller-diameter cylindrical portions, an adapted hole being radially provided in said one of the smaller-diameter cylindrical portions, the first pair of electric conductors passing through the adapted hole and being electrically connected to said one of said smaller-diameter cylindrical portions.

10. The electrocatheter according to claim 7, wherein said ventricular electrode has a substantially cylindrical body inserted in a tubular element inserted in the first end of the first segment, a third shell being provided around the first end of the first segment and around the cylindrical body for sealingly connecting the first end of the first segment to the ventricular electrode, a rounded head extending from said cylindrical body outside the third shell, said head having an inner cavity filled with silicone material, said cylindrical body having an axial dead hole, one of the electric conductors ending in said dead hole and being electrically connected to the cylindrical body.

11. The electrocatheter according to claim 7, wherein one of the electric conductors is connected to the ventricular electrode and defines a first coil and wherein said first pair and a second pair of the electric conductors are connected to the proximal and distal atrial electrodes respectively and are integrated in a second coil, said second coil surrounding the first coil.

12. The electrocatheter according to claim 7 wherein said three-pole connector comprises a body having a cylindrical extension with an axial end pin electrically connected to said ventricular electrode and two conducting rings which are spaced and insulated from one another and from said pin, each of said rings being electrically connected to one of said atrial electrodes.

13. An improved three-pole electrocatheter for permanent cardiac stimulation, comprising:
a flexible body of biocompatible material, comprising a first segment, a second segment and a third segment which extend successively and substantially axially, the first segment defining a first end of the first segment and a second end of the first segment, the second defining a first end of the second segment and a second end of the second segment and the third segment defining a first and a second end of the third segment;
a ventricular electrode provided at the first end of the first segment;
a first shell connecting the second end of the first segment to the first end of the second segment;
a proximal atrial electrode accommodated in the first shell;
a second shell connecting the second end of the second segment to the first end of the third segment;
a distal atrial electrode accommodated in the second shell;
axial holes provided within the first, the second and the third segment;
coaxial coiled insulated electric conductors extending through the axial holes;
a three-pole connector provided at the second end of the third segment and connected to the electrodes by the coiled insulated electric conductors, wherein said ventricular electrode has a substantially cylindrical body inserted in a tubular element inserted in the first end of the first segment, a third shell being provided around the first end of the first segment and around the cylindrical body for sealingly connecting the first end of the first segment to the ventricular electrode, a rounded head extending from said cylindrical body outside the third shell, said head having an inner cavity filled with silicone material, said cylindrical body having an axial dead hole, one of the electric conductors ending in said dead hole and being electrically connected to the cylindrical body of said ventricular electrode.

14. The electrocatheter according to claim 13, wherein said segments are obtained by extrusion from a material selected from the group consisting of medical-grade silicon and polyurethane.

15. Electrocatheter according to claim 13, wherein said proximal atrial electrode has a larger-diameter cylindrical portion which protrudes from the first shell and two smaller-diameter cylindrical portions which extend axially from the larger-diameter cylindrical portion towards the first and the second segments respectively and are contained in the first shell, said cylindrical portions being axially crossed by a hole, a first pair of said electric conductors passing through the hole and ending at one of said smaller-diameter cylindrical portions, an adapted hole being radially provided in said one of the smaller-diameter cylindrical portions, the first pair of electric conductors passing through the adapted hole and being electrically connected to said one of said smaller-diameter cylindrical portions.

16. The electrocatheter according to claim 13, wherein said distal atrial electrode comprises a larger-diameter cylindrical portion which protrudes from the second shell, and two smaller-diameter cylindrical portions which extend axially from the larger-diameter cylindrical portion towards the second and the third segments respectively, and are contained in the second shell, said cylindrical portions being axially crossed by a hole, the coiled insulated electric conductors passing through the hole, an adapted hole being radially provided in one of the smaller-diameter cylindrical portions, a second pair of said conductors passing through the adapted hole and being electrically connected to said one of said smaller-diameter cylindrical portions.

17. The electrocatheter according to claim 13, wherein one of the electric conductors is connected to the ventricular electrode and defines a first coil and wherein a first pair and a second pair of the electric conductors are connected to the proximal and distal atrial electrodes respectively and are integrated in a second coil, said second coil surrounding the first coil.

18. The electrocatheter according to claim 13 wherein said three-pole connector comprises a body having a cylindrical extension with an axial end pin electrically connected to said ventricular electrode and two conducting rings which are spaced and insulated from one another and from said pin, each of said rings being electrically connected to one of said atrial electrodes.

* * * * *